US012704416B2

(12) United States Patent
Namiki et al.

(10) Patent No.: US 12,704,416 B2
(45) Date of Patent: Aug. 11, 2026

(54) TEMPERATURE MEASUREMENT METHOD, TEMPERATURE MEASUREMENT DEVICE, MEDICAL DEVICE SYSTEM, AND LASER TREATMENT METHOD

(71) Applicant: OLYMPUS CORPORATION, Tokyo (JP)

(72) Inventors: Mitsuru Namiki, Tokyo (JP); Ikutoshi Fukushima, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 363 days.

(21) Appl. No.: 18/234,662

(22) Filed: Aug. 16, 2023

(65) Prior Publication Data

US 2023/0392996 A1 Dec. 7, 2023

Related U.S. Application Data

(63) Continuation of application No. PCT/JP2021/009590, filed on Mar. 10, 2021.

(51) Int. Cl.
*G01K 11/32* (2021.01)
*A61B 1/018* (2006.01)
(Continued)

(52) U.S. Cl.
CPC .............. *G01K 11/32* (2013.01); *A61B 18/26* (2013.01); *A61B 1/018* (2013.01);
(Continued)

(58) Field of Classification Search
CPC .......... G01K 11/32; G01K 1/026; G01K 3/12; A61B 18/26; A61B 1/018;
(Continued)

(56) References Cited

U.S. PATENT DOCUMENTS 4,714,342 A 12/1987 Jackson et al.
2013/0271768 A1* 10/2013 Takaoka ............... A61B 1/0669 356/445
(Continued)

FOREIGN PATENT DOCUMENTS

JP S59-230129 A 12/1984
JP 2008-104791 A 5/2008
(Continued)

OTHER PUBLICATIONS

International Search Report dated Jun. 1, 2021 received in PCT/JP2021/009590.
Numajiri, H., et al., "Development of high-accuracy optical-fiber thermometer using fiber bragg grating", Research report, 2011(6), pp. 122-123, Tokyo Metropolitan Industrial Technology Research Institute.
(Continued)

*Primary Examiner* — John E Breene
*Assistant Examiner* — Manuel Salvador Castellon, Jr.
(74) *Attorney, Agent, or Firm* — Scully, Scott, Murphy & Presser, P.C.

(57) ABSTRACT

Provided is a temperature measurement method for measuring an ambient temperature of a long-length medical device, using first and second optical fibers attached to the medical device, the first and second optical fibers extending in parallel with each other along a longitudinal direction of the medical device, and the first optical fiber having a distal end serving as a measurement unit extending beyond a distal end of the second optical fiber along a longitudinal direction of the first and second optical fibers. The method includes: measuring an optical path length difference between a first optical path including the first optical fiber and a second optical path including the second optical fiber; and calculating a temperature of the measurement unit based on the optical path length difference. When temperatures of the first and second optical fibers are uniform, optical path lengths of the first and second optical paths are equal.

20 Claims, 12 Drawing Sheets

(51) Int. Cl.
*A61B 18/00* (2006.01)
*A61B 18/26* (2006.01)

(52) U.S. Cl.
CPC ............... *A61B 2018/00678* (2013.01); *A61B 2018/00696* (2013.01); *A61B 2018/00791* (2013.01)

(58) Field of Classification Search
CPC ........... A61B 2018/00678; A61B 2018/00696; A61B 2018/00791; A61B 2018/00166; A61B 2018/0066; A61B 2018/00708; A61B 2018/00517; A61B 2018/00982; A61B 1/00097; A61B 1/00165; A61B 1/07; A61B 5/01; A61B 2018/00702; A61B 2018/00761; A61B 2018/00785; A61B 2018/263
See application file for complete search history.

(56) References Cited

U.S. PATENT DOCUMENTS

| | | | |
|---|---|---|---|
| 2014/0336637 A1 | 11/2014 | Agrawal et al. | |
| 2019/0328216 A1* | 10/2019 | Beyer ................ | A61B 1/00096 |
| 2020/0300672 A1* | 9/2020 | Kissinger ............... | G01D 5/353 |

FOREIGN PATENT DOCUMENTS

| | | |
|---|---|---|
| JP | 2016-517777 A | 6/2016 |
| JP | 2017-213444 A | 12/2017 |
| WO | 2014/182946 A2 | 11/2014 |

OTHER PUBLICATIONS

Omega Engineering LLC, Tokyo, Japan,“Technical guide—What is a Fiber Optic Temperature Sensor?”, Retrieved from the Internet in Feb. 2021. URL:https://www.jp.omega.com/technical-learning/fiber-optic-temperature-measurement.html.

* cited by examiner 1
4
7
7a
7b
U
U1
9a
2b
8
9b
11
11a
3b
U2
U1+U2
10
10a
10b
5
6
P1
P2
2
3
2a
2c
3a
α

TEMPERATURE MEASUREMENT METHOD, TEMPERATURE MEASUREMENT DEVICE, MEDICAL DEVICE SYSTEM, AND LASER TREATMENT METHOD

CROSS-REFERENCE TO RELATED APPLICATIONS

This is a continuation of International Application PCT/JP2021/009590 which is hereby incorporated by reference herein in its entirety.

TECHNICAL FIELD

The present invention relates to a temperature measurement method, a temperature measurement device, a medical device system, and a laser treatment method.

BACKGROUND ART

Conventional medical devices equipped with temperature sensors are known (see PTL 1, for example). There is a wide variety of temperature sensors such as optical temperature sensors, electrical temperature sensors, infrared temperature sensors, and fiber optic temperature sensors. Optical temperature sensors are best suited for medical devices in terms of measurement accuracy, fineness, and biocompatibility of the material. For example, electrical temperature sensors require a large space and their measurement values are easily fluctuated by external noise such as electromagnetic waves and high frequencies. Infrared temperature sensors have inadequate measurement accuracy, and infrared rays may be interfered with by therapeutic flashes emitted from medical devices, bubbles generated during treatment, etc.

The medical device in PTL 1 is equipped with a fiber Bragg grating (FBG) sensor, one of the optical temperature sensors. The FBG sensor is installed inside an optical fiber that extends along the outer surface of the medical device and measures the ambient temperature of the medical device.

CITATION LIST

Patent Literature

{PTL 1} Japanese Translation of PCT International Application, Publication No. 2016-517777

SUMMARY OF INVENTION

A first aspect of the present invention is a temperature measurement method for measuring an ambient temperature of a long-length medical device, using a first optical fiber and a second optical fiber attached to the medical device, the first optical fiber and the second optical fiber extending in parallel with each other along a longitudinal direction of the medical device, and the first optical fiber having a distal end serving as a measurement unit extending beyond a distal end of the second optical fiber along a longitudinal direction of the first and second optical fibers, the method including: measuring an optical path length difference between a first optical path including the first optical fiber and a second optical path including the second optical fiber; and calculating a temperature of the measurement unit based on the optical path length difference, wherein when temperatures of the first optical fiber and the second optical fiber are uniform, an optical path length of the first optical path and an optical path length of the second optical path are equal.

A second aspect of the present invention is a temperature measurement device that measures an ambient temperature of a long-length medical device, including: a first optical fiber and a second optical fiber that are positioned in the medical device and extend in parallel with each other, the first optical fiber having a distal end serving as a measurement unit extending beyond a distal end of the second optical fiber along a longitudinal direction of the first and second optical fibers; an optical path length difference measuring unit that measures an optical path length difference between a first optical path including the first optical fiber and a second optical path including the second optical fiber; and a processor including hardware configured to calculate a temperature of the measurement unit based on the optical path length difference, wherein when temperatures of the first optical fiber and the second optical fiber are uniform, an optical path length of the first optical path and an optical path length of the second optical path are equal.

A third aspect of the present invention is a laser treatment method including: preparing a medical device equipped with a first optical fiber and a second optical fiber, the first optical fiber and the second optical fiber extending in parallel with each other and the first optical fiber having a distal end serving as a measurement unit extending beyond a distal end of the second optical fiber along a longitudinal direction of the first and second optical fibers; positioning the medical device with respect to a treatment target; projecting a laser beam from the medical device to the treatment target; and measuring an ambient temperature of the medical device, wherein the measuring includes: measuring an optical path length difference between a first optical path including the first optical fiber and a second optical path including the second optical fiber; and calculating a temperature of the measurement unit based on the optical path length difference, and when temperatures of the first optical fiber and the second optical fiber are uniform, an optical path length of the first optical path and an optical path length of the second optical path are equal.

BRIEF DESCRIPTION OF DRAWINGS

FIG. 5 is a diagram for explaining the principle of temperature measurement in the temperature measurement device.

DESCRIPTION OF EMBODIMENTS

First Embodiment

A temperature measurement device and medical device system according to the first embodiment of the present invention will now be described with reference to the drawings.

Figure 1:
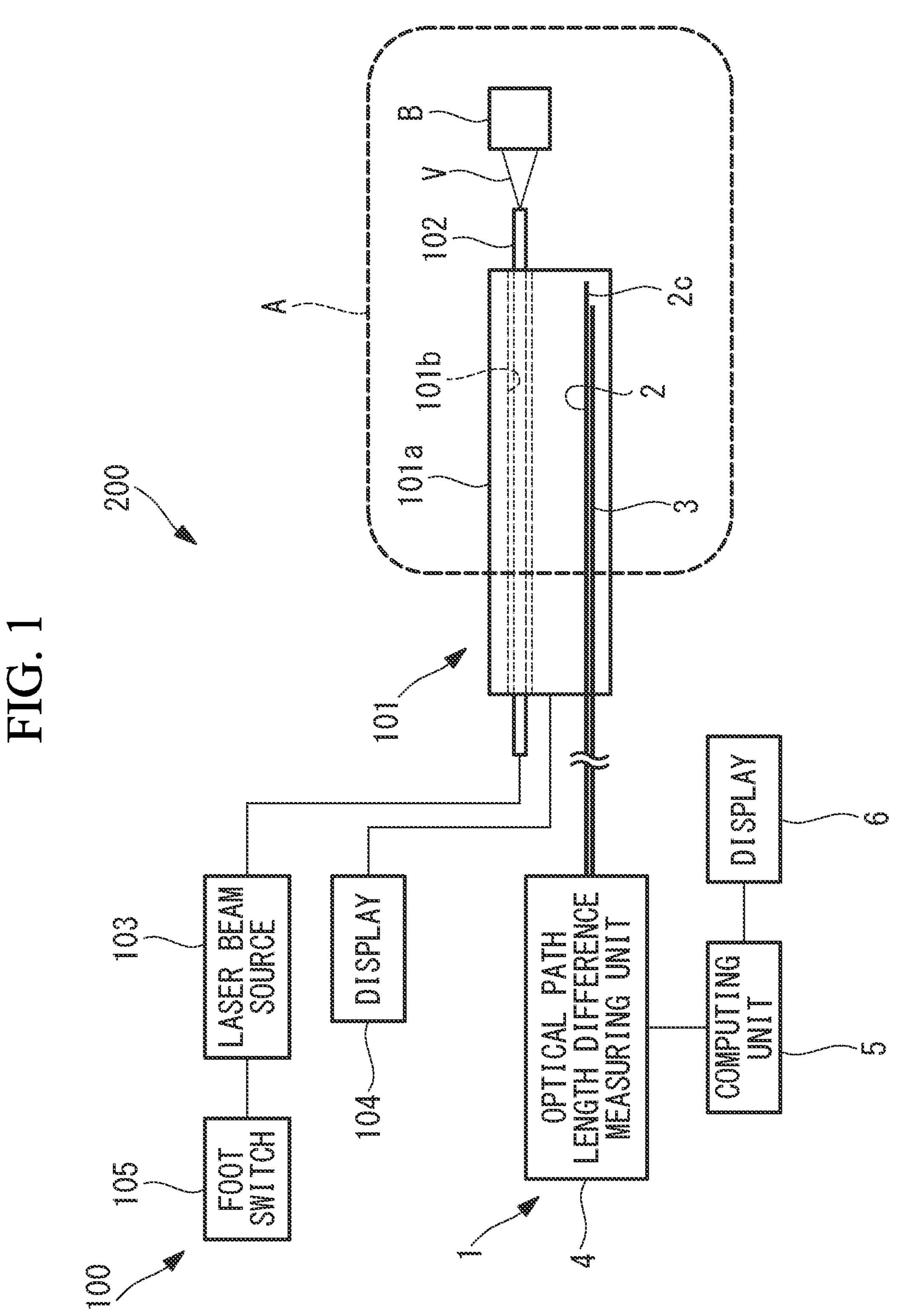
FIG. 1 is an overall configuration diagram of a medical device system according to an embodiment of the present invention.

As shown in FIG. 1, the medical device system 200 is a laser treatment system that treats a treatment target B in a body A with a therapeutic laser beam V. The medical device system 200 includes a medical device 100, which is a laser treatment device.

The medical device 100 includes an endoscope 101, an optical fiber 102, a laser beam source 103, and a display 104. The endoscope 101 is, for example, a soft or rigid ureteroscope. The optical fiber 102 passes through a channel 101*b* in the long insertion portion 101*a* of the endoscope 101, the distal end of the optical fiber 102 protrudes from the distal end of the insertion portion 101*a*, and the proximal end of the optical fiber 102 is connected to the laser beam source 103. The medical device 100 may further include other components such as an image processor and a laser beam control unit, if necessary. The image processor processes endoscopic images, and the laser beam control unit controls the intensity, pulse waveform, frequency, and the like of the laser beam V which is supplied from the laser beam source 103 to the optical fiber 102. The display 104 is an optional display device such as a liquid crystal display. A perfusion device (not shown in the drawing) is provided to supply perfusion fluid to the body A via the channel 101*b*.

After the perfusion device fills the inside of the body A with perfusion fluid, the surgeon emits a laser beam V from the laser beam source 103 by, for example, stepping on a foot switch 105 connected to the laser beam source 103 while observing the endoscope image displayed on the display 104. The laser beam V enters the proximal end of the optical fiber 102 from the laser beam source 103 and is projected from the distal end of the optical fiber 102 onto the treatment target B. In one example, the laser beam V is an infrared laser beam that shatters the treatment target B, a stone. The infrared laser beam V achieves lithotripsy by thermal energy absorbed by water or perfusion fluid in the stone or voids of the stone, and the energy of the emitted laser beam V is stored as thermal energy in the entire body A. In other words, the irradiation with the laser beam V increases the temperature of the entire body A, including the perfusion fluid surrounding the distal end of the insertion portion 101*a*, the endoscope 101, and the optical fiber 102.

The medical device system 200 further includes a temperature measurement device 1 for measuring the temperature around the distal end of the insertion portion 101*a*. The temperature measurement device 1 includes a first optical fiber 2, a second optical fiber 3, an optical path length difference measuring unit 4 that measures the optical path length difference ΔL generated in the two optical paths via the optical fibers 2 and 3, respectively, a computing unit 5 that calculates the temperature based on the optical path length difference ΔL, and a display 6 that displays the temperature. The display 6 is an optional display device, such as a liquid crystal display, and may be common to the display 104.

Figure 2:
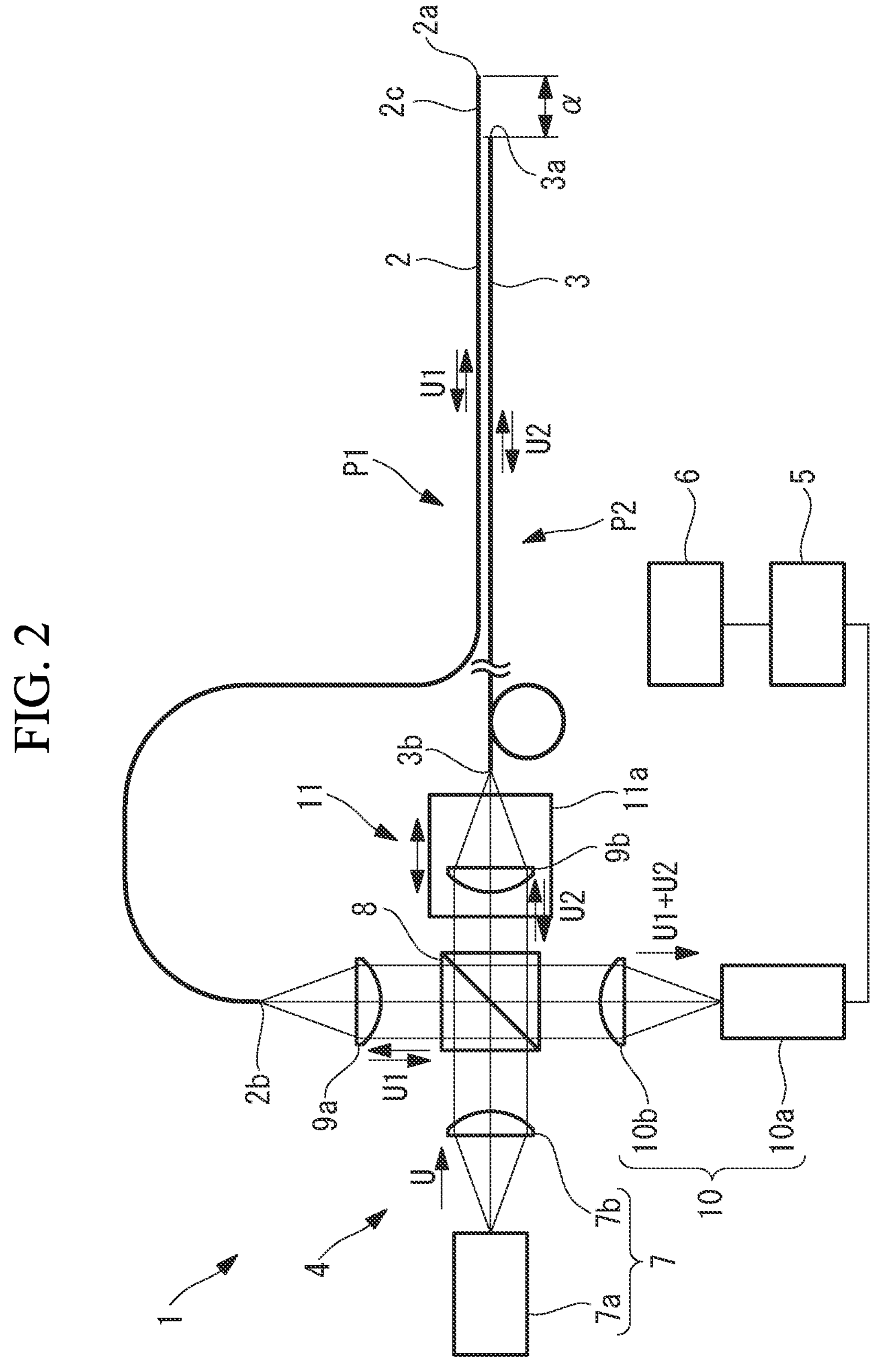
FIG. 2 is an overall configuration diagram of a temperature measurement device according to a first embodiment of the present invention.

FIG. 2 shows the specific configuration of the temperature measurement device 1.

Each of the optical fibers 2 and 3 is a single-mode fiber having a cladding diameter of 125 μm, for example. The lengths of the two optical fibers 2 and 3 are equal or approximately equal. The two optical fibers 2 and 3 are close to each other in the radial direction of the optical fibers 2 and 3, extend in parallel along the longitudinal direction of the insertion portion 101*a*, and are attached to the side surface of the insertion portion 101*a*. The distal ends 2*a* and 3*a* of the two optical fibers 2 and 3 are located in the vicinity of the distal end of the insertion portion 101*a*, and the distal end 2*a* of the first optical fiber 2 is longer by a length a along the longitudinal direction of the optical fibers 2 and 3 than the distal end 3*a* of the second optical fiber 3. The distal end of the length a of the first optical fiber 2 is a measurement unit 2*c*, and the computing unit 5 calculates the temperature change amount T and temperature of the measurement unit 2*c* as described below.

The optical path length difference measuring unit 4 measures the optical path length difference ΔL between a first optical path P1 including the first optical fiber 2 and a second optical path P2 including the second optical fiber 3. To be specific, the optical path length difference measuring unit 4 includes a light source unit 7, a split-and-combine unit 8, two couplers 9*a* and 9*b*, a detection unit 10, and an optical path length adjustment mechanism 11.

The light source unit 7 has a low-coherence light source 7*a* that emits low-coherence light, which is measurement light U, and a collimating lens 7*b* that forms the measurement light U into collimated light.

The split-and-combine unit 8 is a spatial optical system, such as a beam splitter, and is positioned between the light source unit 7 and the proximal ends 2*b* and 3*b* of the two optical fibers 2 and 3. The split-and-combine unit 8 splits the measurement light U incident from the light source unit 7 into measurement light U1 traveling along the first optical path P1 and second measurement light traveling along the second optical path P2. The split-and-combine unit 8 also combines the first measurement light U1 that has reciprocated along the first optical path P1 and the second measurement light U2 that has reciprocated along the second optical path P2.

The first optical path P1 is the optical path between the split-and-combine unit 8 and the distal end 2*a* of the first optical fiber 2. In other words, the first measurement light U1 returns to the split-and-combine unit 8 from the split-and-combine unit 8 via the coupler 9*a*, proximal end 2*b*, distal end 2*a*, proximal end 2*b*, and coupler 9*a* in this order.

The second optical path P2 is the optical path between the split-and-combine unit 8 and the distal end 3*a* of the second optical fiber 3. In other words, the second measurement light U2 returns to the split-and-combine unit 8 from the split-and-combine unit 8 via the coupler 9*b*, proximal end 3*b*, distal end 3*a*, proximal end 3*b*, and coupler 9*b* in this order.

A reflective surface may be provided at each of the distal ends 2*a* and 3*a* to increase the reflectivity of the measurement light U1 and U2 at the distal ends 2*a* and 3*a*.

The couplers 9*a* and 9*b* are disposed between the split-and-combine unit 8 and the proximal ends 2*b* and 3*b* of the optical fibers 2 and 3, respectively, and optically couple the split-and-combine unit 8 and each of the proximal ends 2*b* and 3*b*. To be specific, the couplers 9*a* and 9*b* are convex lenses. The coupler 9*a* focuses the first measurement light U1, which is collimated light incident from the split-and-combine unit 8, to the proximal end 2*b*, and the coupler 9*b* focuses the second measurement light U2, which is collimated light incident from the split-and-combine unit 8, to the proximal end 3*b*.

The detection unit 10 includes a photodetector 10*a* that detects the interference intensity of the combined light U1+U2 of the measurement light U1 and the measurement light U2 combined by the split-and-combine unit 8. The detection unit 10 may further include a lens 10*b* disposed between the split-and-combine unit 8 and the photodetector 10*a* to focus the combined light U1+U2 onto the photodetector 10*a*.

The optical fibers 2 and 3 have mutually identical optical characteristics, the couplers 9*a* and 9*b* have mutually identical optical characteristics, and the optical path length L1 of the first optical path P1 and the optical path length L2 of the second optical path P2 are designed to be equal. In practice, however, it is not easy to make the two optical path lengths L1 and L2 equal with wavelength-order accuracy due to errors in the lengths of the optical fibers 2 and 3 and the like.

The optical path length adjustment mechanism 11 fine-tunes at least one of the optical path length L1 and the optical path length L2 with wavelength-order precision. The optical path length adjustment mechanism 11 has a fine movement stage 11*a* that can be moved along the longitudinal direction of the second optical fiber 3 with a resolution of a wavelength order. The coupler 9*b* and the proximal end of the second optical fiber 3 are fixed to the fine movement stage 11*a*, and the fine movement stage 11*a*, the coupler 9*b*, and the proximal end of the second optical fiber 3 move together. Consequently, the fine movement of the fine movement stage 11*a* can slightly change the distance d between the split-and-combine unit 8 and the coupler 9*b*, thereby fine-tuning the optical path length L2. The fine movement stage 11*a* can be either manual or motorized. In the case where it is motorized, the optical path length adjustment mechanism 11 further includes a motor (not shown in the drawings) that drives the fine movement stage 11*a*.

The aforementioned configuration of the optical path length adjustment mechanism 11 is merely one example, and the optical path length adjustment mechanism 11 may adjust the optical path length by other means. To give other examples, the optical path length adjustment mechanism 11 may be configured to adjust the optical path length by changing the thickness of a medium having one or more refractive indices. For example, the optical path length adjustment mechanism 11 may have two prisms whose sides are right-angled triangles and whose slopes face each other, and the thickness (optical path length difference) may be made variable by increasing or decreasing the overlap of the slopes of the two prisms.

Figure 3A:
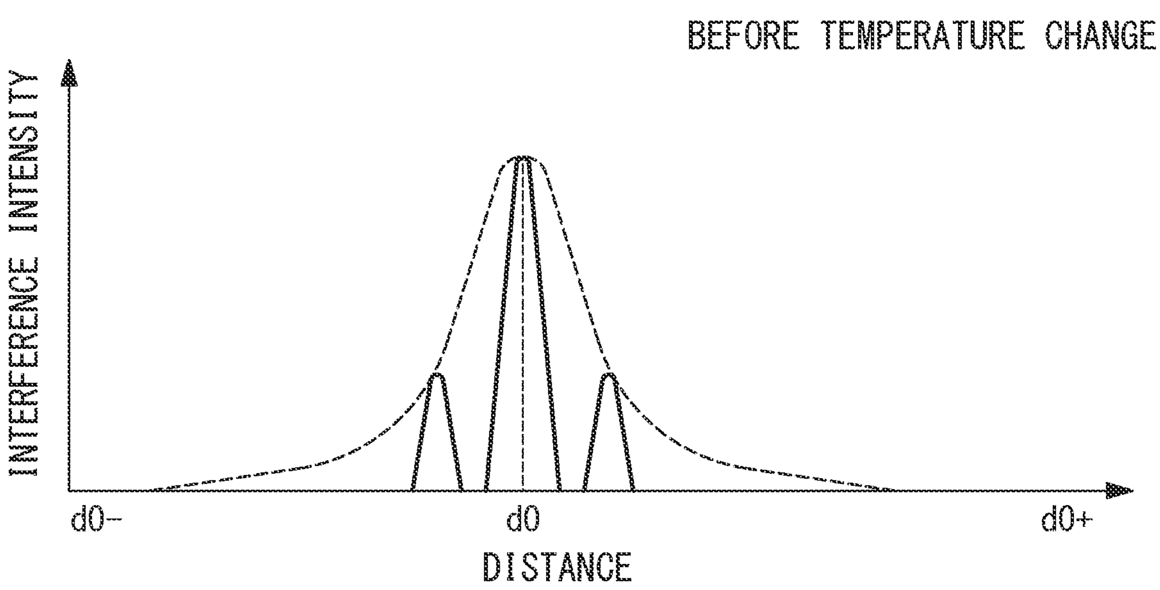
FIG. 3A is a diagram showing the relationship between the distance between a split-and-combine unit and a coupler and the interference intensity before temperature change.

The wavelength of the first measurement light U1 and the wavelength of the second measurement light U2 are equal. In addition, the phase of the first measurement light U1 and the phase of the second measurement light U2 are identical at the split-and-combine unit 8, which is the starting point of the optical paths P1 and P2. For this reason, when the optical path lengths L1 and L2 are equal, as shown in FIG. 3A, the interference intensity distribution is generated by the mutual interference and mutual intensification of the two types of combined measurement light U1 and U2, and the interference intensity of the combined light U1+U2 detected by the photodetector 10*a* becomes high. Therefore, the optical path length L2 can be adjusted to the same length as the optical path length L1 by determining the distance d to be the reference distance d0 at which the interference intensity peaks.

The optical path length adjustment mechanism 11 may be configured to adjust the optical path length L1 instead of the optical path length L2, or to adjust both the optical path length L1 and the optical path length L2.

Figure 3B:
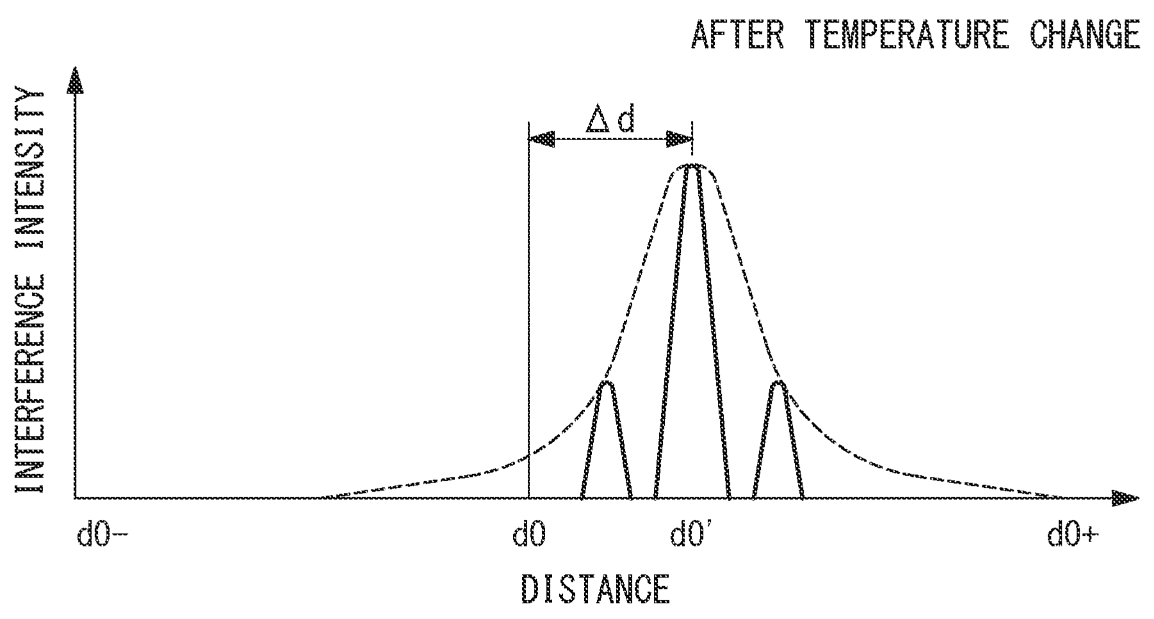
FIG. 3B is a diagram showing the relationship between the distance between the split-and-combine unit and the coupler and the interference intensity after temperature change.

Here, when a temperature gradient is generated in optical fibers 2 and 3 due to a temperature change around the insertion portion 101*a*, the first optical path length L1 and the second optical path length L2 change. In this case, as explained later, an optical path length difference ΔL=|L1−L2| is generated according to the temperature change amount T of the measurement unit 2*c*, and the distance d at which interference occurs changes from the reference distance d0 by the amount of the optical path length difference ΔL. The reference distance d0 is the distance d at which the interference intensity peaks when the temperatures of the optical fibers 2 and 3 are uniform before the temperature change occurs in the insertion portion 101*a*. To be specific, as shown in FIG. 3B, when the temperature of the measurement unit 2*c* rises, the distance d at which interference occurs becomes larger than the reference distance d0, and when the temperature of the measurement unit 2*c* falls, the distance d at which interference occurs becomes smaller than the reference distance d0. Accordingly, the amount of temperature change T of the measurement unit 2*c* can be estimated from the amount of change Δd of the distance d at which interference occurs, from the reference distance d0. In FIGS. 3A and 3B, the horizontal axis represents the distance d between the split-and-combine unit 8 and the coupler 9*b*, and the vertical axis represents the intensity of the combined light U1+U2 detected by the photodetector 10*a*.

Figure 4:
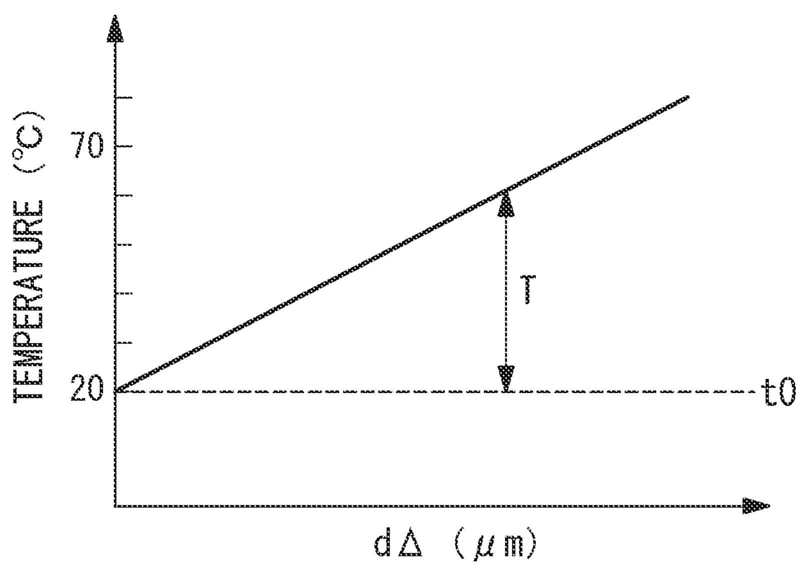
FIG. 4 is a graph showing an example of the relationship between the amount of change in optical path length and the temperature of a measurement unit.

As shown in FIG. 4, the computing unit 5 stores an equation or table showing the relationship between the amount of change Δd and the amount of temperature change T. The equation or table is experimentally obtained. The computing unit 5 obtains the amount of change Δd and the corresponding amount of temperature change T from the equation or table. The vertical axis in FIG. 4 represents the temperature t of the measurement unit 2*c* calculated using the amount of temperature change T. The computing unit 5 may calculate the current temperature t of the measurement unit 2*c* by adding the amount of temperature change T to the temperature t0 of the measurement unit 2*c* which is obtained before the temperature change. The temperature t0 before the temperature change is, for example, the measured temperature of the optical fibers 2 and 3 before the insertion portion 101*a* is inserted into the body A, or the measured temperature of the temperature invariant region of the optical fibers 2 and 3 which is obtained after the insertion portion 101*a* is inserted into the body A.

The computing unit 5 includes a processor, such as a central processing unit, and a memory that stores equations or tables, and the aforementioned process in the computing unit 5 is performed by the processor.

The principle of measuring temperature with the temperature measurement device 1 will now be explained.

Figure 5:
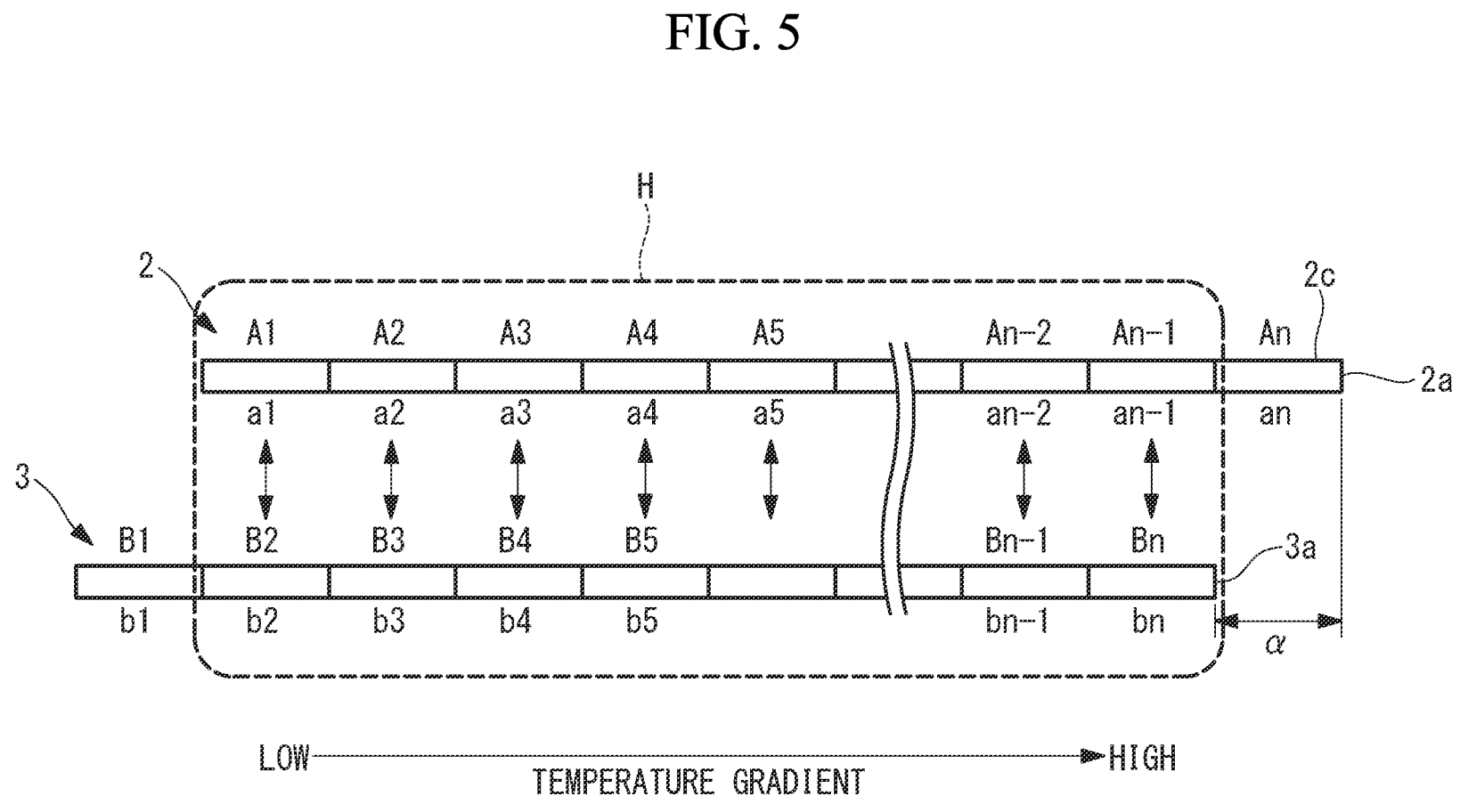

As shown in FIG. 5, a portion of the two optical fibers 2 and 3 is located in the temperature variant region H. The temperature variant region H is a region where a common temperature change occurs in the two optical fibers 2 and 3 during use of the medical device 100, and is specifically a region on the distal end side that is inserted into the body A. The length of the portion of the first optical fiber 2 located in the temperature variant region H and the length of the portion of the second optical fiber 3 located in the temperature variant region H are equal. The proximal end side of the temperature variant region H (left side in FIG. 5) is a temperature invariant region where no temperature change occurs in the optical fibers 2 and 3 during use of the medical device 100, and is specifically the proximal side region that is located outside the body.

The first optical fiber 2 in the temperature variant region H is divided equally into regions having the length a that is equal to the length of the measurement unit 2*c*, thereby forming n regions A1, A2, . . . , An, including the measurement unit 2*c*. The region An which is the region closest to the distal end is the measurement unit 2*c*. Similarly, the second optical fiber 3 in the temperature variant region H is divided equally into regions having the length a, thereby forming n regions B1, B2, . . . , Bn. The region Bn which is the region closest to the proximal end is a part of the temperature invariant region outside of the temperature variant region H.

The optical response values ai and bi for the regions Ai and Bi (I=1, 2, . . . , n) will now be considered. The optical response values represent changes in thermal expansion and refractive index caused by temperature change. The sums S1 and S2 of the round trip of the optical response values ai and bi in the temperature variant region H are expressed as follows. S1 is the sum of the optical response values ai of the first optical fiber 2 and S2 is the sum of the optical response values bi of the second optical fiber 3.

$$S1 = 2\sum_{i=1}^{n} ai,\ \ S2 = 2\sum_{i=1}^{n} bi$$

Here, as shown in FIG. 5, a temperature gradient occurs in the optical fibers 2 and 3 in the longitudinal direction. In addition, the region Ai and region Bill are close to each other along the radial axis of the optical fibers 2 and 3. Therefore, the optical response value ai of the region Ai and the optical response value bill of the region Bill are equal. Accordingly, the difference ΔS between the sum S1 of the optical response value ai of the first optical fiber 2 and the sum S2 of the optical response value bi of the second optical fiber 3 is as expressed by the following equation.

$$\Delta S = S1 - S2 = 2\sum_{i=1}^{n} ai - 2\sum_{i=1}^{n} bi = an - b1$$

The optical path length of the optical fibers 2 and 3 due to temperature change is changed by a change in refractive index and a change in the length of optical fibers 2 and 3 due to thermal expansion. Therefore, the sums S1 and S2 correspond to the amounts of change in optical path lengths L1 and L2 due to temperature change, respectively, and ΔS corresponds to the optical path length difference ΔL caused by temperature change. In addition, an-b1 corresponds to the amount of change in the temperature of the measurement unit 2C with respect to the temperature of the temperature invariant region. Therefore, the optical path length difference ΔL corresponds to the amount of optical path length change and the amount of temperature change in the measurement unit 2*c*, and the amount of temperature change in the measurement unit 2*c* can be estimated from the optical path length difference ΔL.

The amount of change in refractive index ΔN of the optical fibers 2 and 3 due to a temperature change of 1° C. is $1\times10^{-5}$° C. In other words, the amount of change in the optical path length of the measurement unit 2*c* of the length a due to a temperature change of 1° C. is α×ΔN. For example, the amount of change in the optical path length of the measurement unit 2*c* due to a temperature change of 1° C. is 10 μm when α=1 m, 1 μm when α=10 cm, and 0.1 μm when α=10 mm. Since the measurement light U1 travels back and forth through the measurement unit 2*c*, the amount of optical path length change that occurs in the measurement unit 2*c* is twice (α×ΔN). When the wavelength of the measurement light U1 is 0.4 μm, even if α=10 mm, a change in temperature of 1° C. produces an optical path length change of half a wavelength of the measurement light U1.

To generate a change in optical path length, which corresponds to the wavelength of the measurement light U1, in the measurement unit 2*c* with a change in refractive index and thermal expansion, the following equation (1) must be satisfied. Aa is the amount of change in the length a of the measurement unit 2*c* due to thermal expansion.

$$(\Delta N \times \alpha + N \times \Delta\alpha) \times \Delta T \times 2 \approx \lambda \tag{1}$$

Since the change in the refractive index is sufficiently larger than the thermal expansion, Equation (1) can be rewritten as Equation (2) if we focus only on the change in the refractive index.

$$\Delta N \times \alpha \times \Delta T \times 2 \approx \lambda \tag{2}$$

If the amount of temperature change T is measured with an accuracy ΔT of 1/10, α=20/ΔT based on Equation (2). Here, $\Delta N \approx 1\times10^{-5}$ and $\lambda = 0.4\times10^{-3}$. Therefore, when the amount of temperature change T is 5, 20, 50, 100, or 1000, the length a of the measurement unit 2*c* is as follows.

| Temperature change T (° C.) | Accuracy ΔT (° C.) | Length α (mm) |
|---|---|---|
| 5 | 0.5 | 40 |
| 20 | 2 | 10 |
| 50 | 5 | 4 |
| 100 | 10 | 2 |
| 1000 | 100 | 0.2 |

For example, in treatment in which stones are crushed by a laser beam, when the fact that the body temperature changes by 20° C. from 37° C. is to be noted, a 20° C. temperature change can be measured with an accuracy of 2° C. by designing the length a of the measurement unit 2*c* to be 10 mm. In industrial applications, when measuring temperature changes of hundreds or thousands of degrees, the desired temperature change can be measured with the desired accuracy by adjusting the length a within the confines of the temperature tolerance of the optical fiber.

A laser treatment method using the laser treatment system 200 will now be explained.

Figure 6:
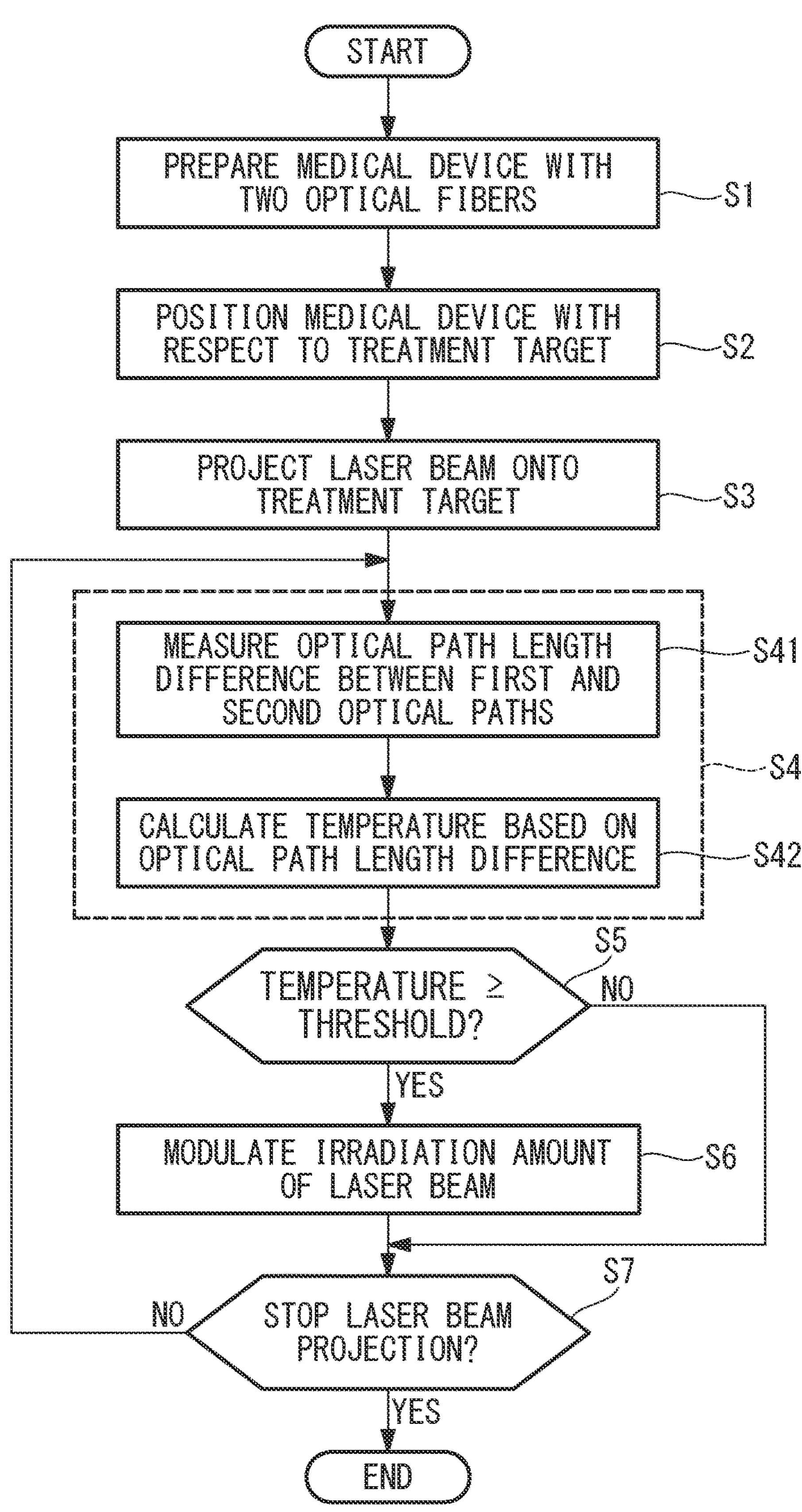
FIG. 6 is a flowchart showing a laser treatment method.

As shown in FIG. 6, the laser treatment method includes Step S1 of preparing a medical device 100 with two optical fibers 2 and 3, Step S2 of positioning the medical device 100 with respect to the treatment target B, Step S3 of projecting a therapeutic laser beam from the medical device 100 toward the treatment target B, and Step S4 of measuring the ambient temperature of the medical device 100.

In Step S1, while the temperature of the optical fibers 2 and 3 is uniform over the entire length, the two optical path lengths L1 and L2 are adjusted to the same length with the optical path length adjustment mechanism 11, and the optical path length difference ΔL is adjusted to zero. To be specific, measurement light U is emitted from the light source 7*a*, and the fine movement stage 11*a* is moved while the interference intensity of the combined light U1+U2 detected by the photodetector 10*a* is being observed, and the distance d is determined to be the reference distance d0 at which the interference intensity peaks. The optical path lengths L1 and L2 are adjusted either by manual operation of the fine movement stage 11*a* by a surgeon or other operators, or by automatic control of the fine movement stage 11*a* by a control device, which is not shown in the drawings, based on the interference intensity.

Next, in Step S2, the surgeon inserts the insertion portion 101*a* into the patient's body A and simultaneously fills the body A with perfusion fluid with the perfusion device, and positions the distal end of the insertion portion 101*a* in the vicinity of the treatment target B. For example, the distal end of the insertion portion 101*a* is positioned in the vicinity of the stone B in the ureter.

Next, in Step S3, the surgeon turns on a foot switch 105 by stepping on the foot switch 105 to emit the therapeutic laser beam V from the laser beam source 103. The laser beam V is projected from the distal end of the optical fiber 102 onto the treatment target B, so that the treatment target B is treated. For example, the projection of the laser beam V crushes the stone B. Continuously projecting the laser beam V onto the treatment target B allows the residual energy of the emitted optical energy to accumulate as thermal energy throughout the perfusion fluid present in the body A, the endoscope 101, and the optical fiber 102, resulting in a temperature increase at and around the distal end of the optical fiber 102.

While the laser beam V is being projected onto the treatment target B, Step S4, which is the temperature measurement method according to this embodiment, is performed. As shown in FIG. 6, Step S4 includes Step S41 of measuring the optical path length difference ΔL between the first optical path P1 and the second optical path P2, and Step S42 of calculating the temperature of the measurement unit 2*c* based on the optical path length difference ΔL.

In Step S41, the optical path length difference ΔL is measured based on the interference between the first measurement light U1 that has reciprocated along the first optical path P1 and the second measurement light U2 that has reciprocated along the second optical path P2.

To be specific, the measurement light U1 and U2 enter the first optical path P1 and the second optical path P2 from the light source unit 7 via the split-and-combine unit 8. The first measurement light U1 reciprocates along the first optical path P1 and returns to the split-and-combine unit 8. The second measurement light U2 reciprocates along the second optical path P2 and returns to the split-and-combine unit 8. The combined light U1+U2 of the first measurement light U1 and the second measurement light U2, which are combined by the split-and-combine unit 8, enters the photodetector 10*a*.

When the temperature of the part of the insertion portion 101*a* that is positioned inside the body A changes from before the insertion portion 101*a* was inserted into the body A, both the optical path length L1 of the first optical path P1 and the optical path length L2 of the second optical path P2 change. At this time, the amount of change in optical path length L1 and the amount of change in optical path length L2 differ from each other due to the fact that the measurement unit 2*c*, which is the distal end of the first optical fiber 2, extends beyond the distal end of the second optical fiber, resulting in an optical path length difference ΔL.

To detect the optical path length difference ΔL, the second optical path length L2 is changed using the optical path length adjustment mechanism 11, and the amount of change Δd in the optical path length L2 at which interference between the first measurement light U1 and second measurement light U2 occurs is detected. To be specific, the distance d between the split-and-combine unit 8 and the coupler 9*b* is changed between the distance d- and the distance d+ by moving the fine movement stage 11*a*, to detect the distance d0' at which the interference intensity of the combined light U1+U2 detected by the photodetector 10*a* peaks, thereby detecting the amount of change Δd in distance d0' from the reference distance d0. The distance −d is smaller than the distance d0 and the distance d+ is larger than the distance d0.

Next, in Step S42, the amount of temperature change T in the measurement unit 2*c* corresponding to the amount of change Δd is calculated using the computing unit 5, and the current temperature of the measurement unit 2*c* is calculated based on the amount of temperature change T and the temperature of the measurement unit 2*c* observed before insertion. The calculated amount of temperature change T and the current temperature are displayed on the display 6.

Continuously projecting the laser beam V onto the treatment target B increases the temperature at and around the distal end of the optical fiber 102. To prevent excessive temperature increase, the laser treatment method may further include Step S5 of comparing the temperature of the measurement unit 2*c* with a predetermined threshold, and if the temperature is equal to or more than the predetermined threshold (YES in Step S5), Step S6 of modulating the irradiation amount of the laser beam V projected onto the treatment target B. The modulation of the irradiation amount includes, for example, increasing, reducing, or modulating at least one of the peak power, pulse width, and repetition frequency of a pulsed laser beam V.

The surgeon observes the current temperature of the measurement unit 2*c* displayed on the display 6, and when the temperature exceeds a predetermined threshold, he or she reduces the amount of irradiation by modulating the amount of irradiation. For example, the surgeon stops the projection of the laser beam V by turning off the foot switch 105. Instead of stopping the projection of the laser beam V, the surgeon may change the position of the optical fiber 102. For example, in Step S6, the surgeon may move the optical fiber 102 radially by moving the insertion portion 101*a* radially. This allows the target spot of projection of the laser beam V to be changed to prevent excessive temperature increase due to continued projection of the laser beam V onto the same spot. Alternatively, the surgeon may move the optical fiber 102 away from the treatment target B by retracting the insertion portion 101*a* or the optical fiber 102 toward the proximal end. This can weaken the intensity of the laser beam V projected onto the treatment target B.

The laser treatment method may further include the step of re-modulating the amount of irradiation of the laser beam V if, after Step S6, the measured temperature drops below a predetermined threshold (YES in Step S5). For example, the surgeon increases the amount of irradiation by modulating the amount of irradiation. The modulation of the amount of irradiation also includes, for example, modulating at least one of the peak power, pulse width, and repetition frequency of a pulsed laser beam V. The modulation of the amount of irradiation may be performed by the surgeon manually operating the light source 103 or by a control device, not shown in the drawing, automatically controlling the light source 103.

Thus, the temperature measurement device 1 of this embodiment measures the temperature at and around the distal end of the insertion portion 101*a*, using two optical fibers 2 and 3 positioned outside the insertion portion 101*a*. The accuracy of temperature measurement is determined by the length a of the measurement unit 2*c*, which is barely affected by deformation of the optical fibers 2 and 3. Accordingly, appropriately designing the length a of the measurement unit 2*c* allows the desired high measurement accuracy to be easily achieved, thereby accurately measuring the temperature change and temperature at and around the distal end of the insertion portion 101*a*.

In addition, since generally-used optical fibers can be used as the optical fibers 2 and 3, higher measurement accuracy can be achieved with a less expensive configuration than when optical fibers with FBGs are used.

The thin optical fibers 2 and 3 can be added to the medical device 100 with little or no increase in the outer diameter of the medical device 100. Thus, the temperature measurement device 1 can be suitably mounted on the medical device 100 with a small diameter.

Second Embodiment

A temperature measurement device and medical device system according to the second embodiment of the present invention will now be described. In this embodiment, the same components as in the first embodiment will be denoted by the same reference numerals as the corresponding ones, and explanations thereof will be omitted.

Figure 7:
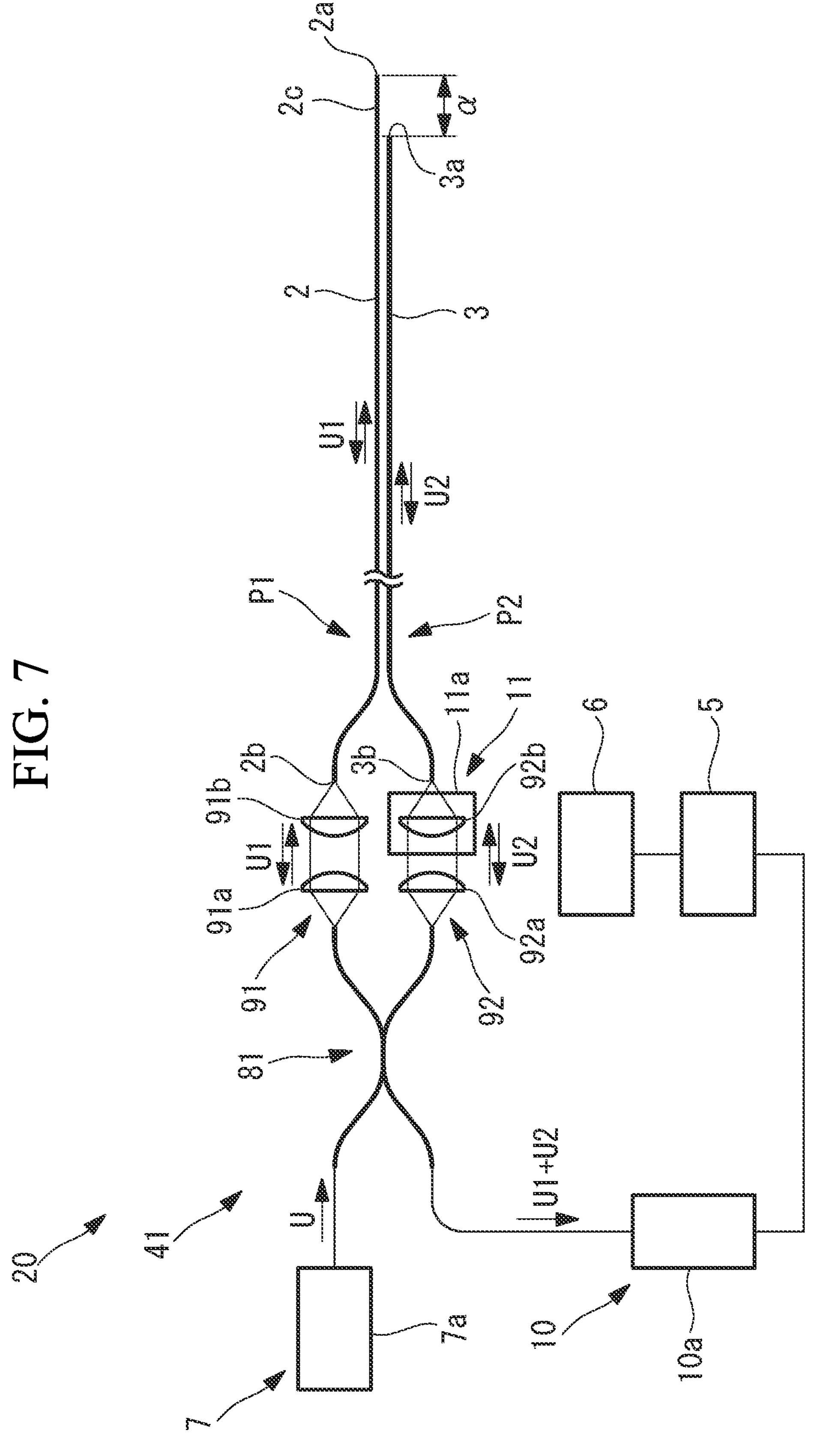
FIG. 7 is an overall configuration diagram of a temperature measurement device according to a second embodiment of the present invention.

The medical device system of this embodiment includes a medical device 100 and a temperature measurement device 20. As shown in FIG. 7, the temperature measurement device 20 differs from the temperature measurement device 1 in that it has an optical path length difference measuring unit 41 instead of an optical path length difference measuring unit 4.

The temperature measurement device 20 includes a first optical fiber 2, a second optical fiber 3, an optical path length difference measuring unit 41 for measuring the optical path length difference $\Delta L$, a computing unit 5, and a display 6.

The optical path length difference measuring unit 41 includes a light source unit 7, a split-and-combine unit 81, two couplers 91 and 92, a detection unit 10, and an optical path length adjustment mechanism 11.

The split-and-combine unit 81 is an optical fiber coupler and is positioned between the light source unit 7 and the proximal ends 2*b* and 3*b* of the two optical fibers 2 and 3. The split-and-combine unit 81 splits the measurement light U incident from the light source unit 7 into measurement light U1 traveling along the first optical path P1 and second measurement light U2 traveling along the second optical path P2. The split-and-combine unit 8 also combines the first measurement light U1 that has reciprocated along the first optical path P1 and the second measurement light U2 that has reciprocated along the second optical path P2.

To be specific, the optical fiber coupler 81 has two input ports and two output ports. One input port is connected to the light source unit 7, and the other input port is connected to the detection unit 10. One output port is connected to the proximal end 2*b* via the first coupler 91, and the other output port is connected to the proximal end 3*b* via the second coupler 92.

The coupler 91 optically couples one output port to the proximal end 2*b*, and the coupler 92 optically couples the other output port to the proximal end 3*b*. To be specific, the coupler 91 has a first lens 91*a* located on the split-and-combine unit 81 side and a second lens 91*b* located on the optical fiber 2 side. The coupler 92 has a first lens 92*a* located on the split-and-combine unit 81 side and a second lens 92*b* located on the optical fiber 3 side. The first lenses 91*a* and 92*a* convert the measurement light U1 and U2 emitted from the split-and-combine unit 81 into collimated light, respectively, and the second lenses 91*b* and 92*b* focus the collimated light onto the proximal ends 2*b* and 3*b*, respectively.

The first optical path P1 is the optical path between the split-and-combine unit 81 and the distal end 2*a* of the first optical fiber 2. In other words, the first measurement light U1 returns to the split-and-combine unit 81 from the split-and-combine unit 81 via the coupler 91, the proximal end 2*b*, the distal end 2*a*, the proximal end 2*b*, and the coupler 91 in this order.

The second optical path P2 is the optical path between the split-and-combine unit 81 and the distal end 3*a* of the second optical fiber 3. In other words, the second measurement light U2 returns to the split-and-combine unit 81 from the split-and-combine unit 81 via the coupler 92, the proximal end 3*b*, the distal end 3*a*, the proximal end 3*b*, and the coupler 92, in this order.

The second lens 92*b* of the coupler 92 and the proximal end of the second optical fiber 3 are fixed to the fine movement stage 11*a* of the optical path length adjustment mechanism 11, and the fine movement stage 11*a*, the second lens 92*b*, and the proximal end of the second optical fiber 3 move together. Accordingly, the distance d between the split-and-combine unit 81 and the second lens 92*b* can be slightly changed by the fine movement of the fine movement stage 11*a*, thereby fine-tuning the optical path length L2.

Other configurations, actions, and effects of the temperature measurement device 20 are the same as those of the temperature measurement device 1, and the description thereof will therefore be omitted.

Third Embodiment

The temperature measurement device and medical device system according to the third embodiment of the present invention will now be described. In this embodiment, the same components as in the first embodiment will be denoted by the same reference numerals as the corresponding ones, and explanations thereof will be omitted.

Figure 8:
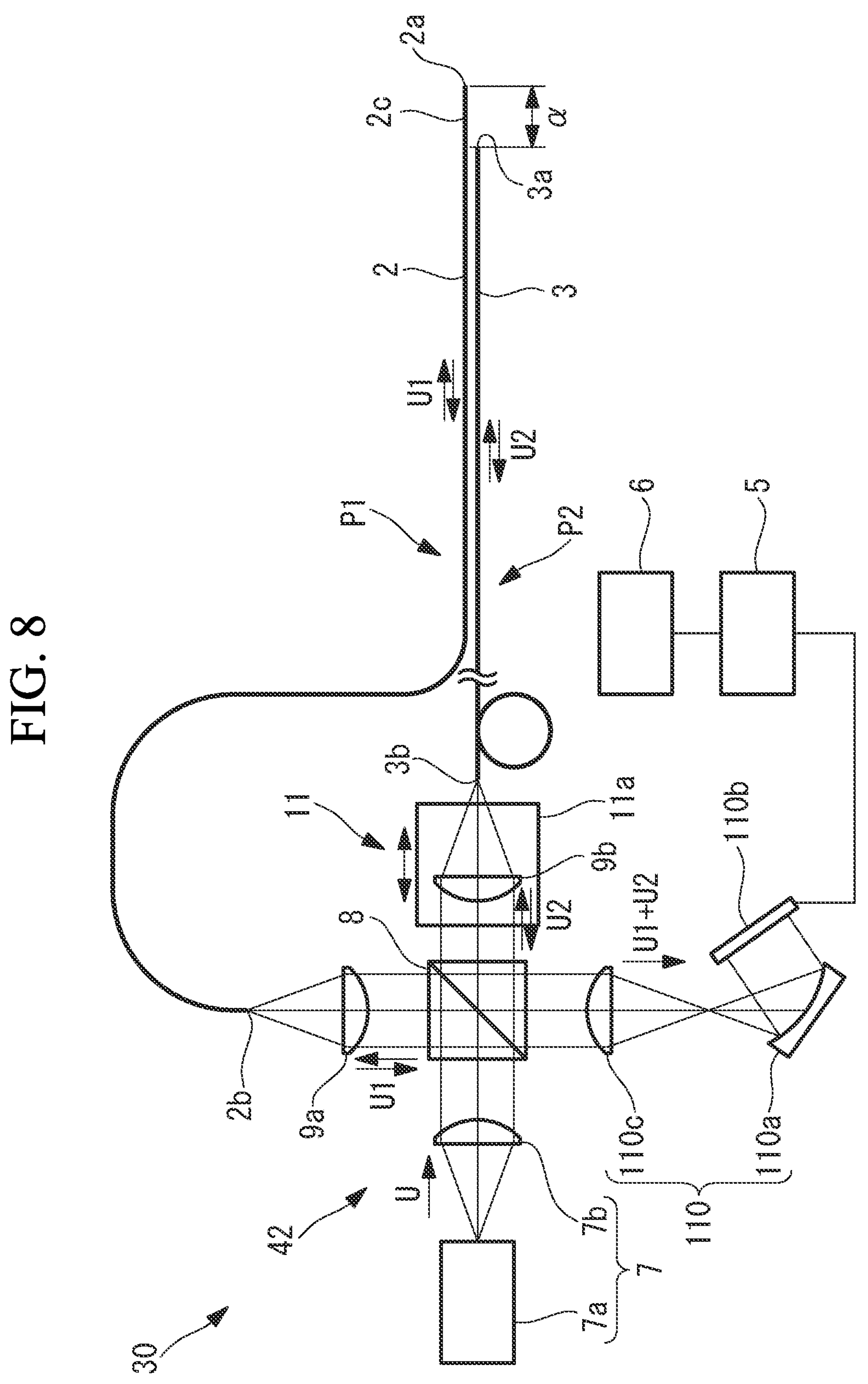
FIG. 8 is an overall configuration diagram of a temperature measurement device according to a third embodiment of the present invention.

The medical device system according to this embodiment includes a medical device 100 and a temperature measurement device 30. As shown in FIG. 8, the temperature measurement device 30 differs from the temperature measurement device 1 in that it has a detection unit 110 instead of a detection unit 10.

The temperature measurement device 30 includes a first optical fiber 2, a second optical fiber 3, an optical path length difference measuring unit 42, a computing unit 5, and a display 6.

The optical path length difference measuring unit 42 includes a light source unit 7, a split-and-combine unit 8, two couplers 9*a* and 9*b*, a detection unit 110, and an optical path length adjustment mechanism 11.

The detection unit 110 includes a spectrometer that spectrally splits combined light U1+U2 and detects the intensity of combined light U1+U2 at each wavelength. To be specific, the spectrometer consists of a diffraction grating 110*a* that spectrally splits combined light U1+U2, and a linear sensor 110*b* that is positioned in the direction of the wavelength of the combined light U1+U2 that has been spectrally split and detects the light intensity at each wavelength.

The detection unit 110 includes a lens 110*c* positioned between the split-and-combine unit 8 and the diffraction grating 110*a*, and the lens 110*c* may focus the combined light U1+U2 between the split-and-combine unit 8 and the diffraction grating 110*a*.

Figure 9A:
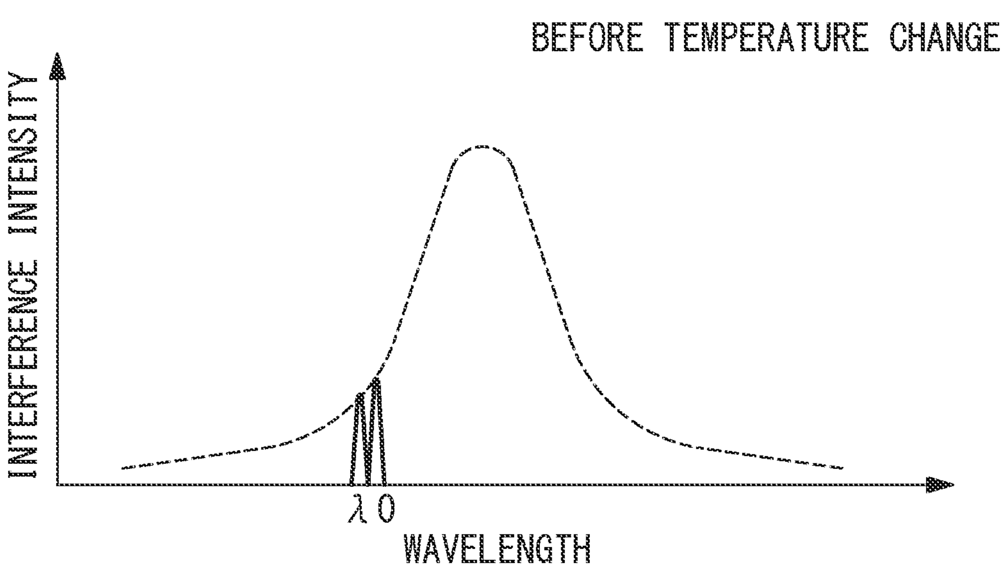
FIG. 9A is a graph showing the relationship between the wavelength and the interference intensity before temperature change.
Figure 9B:
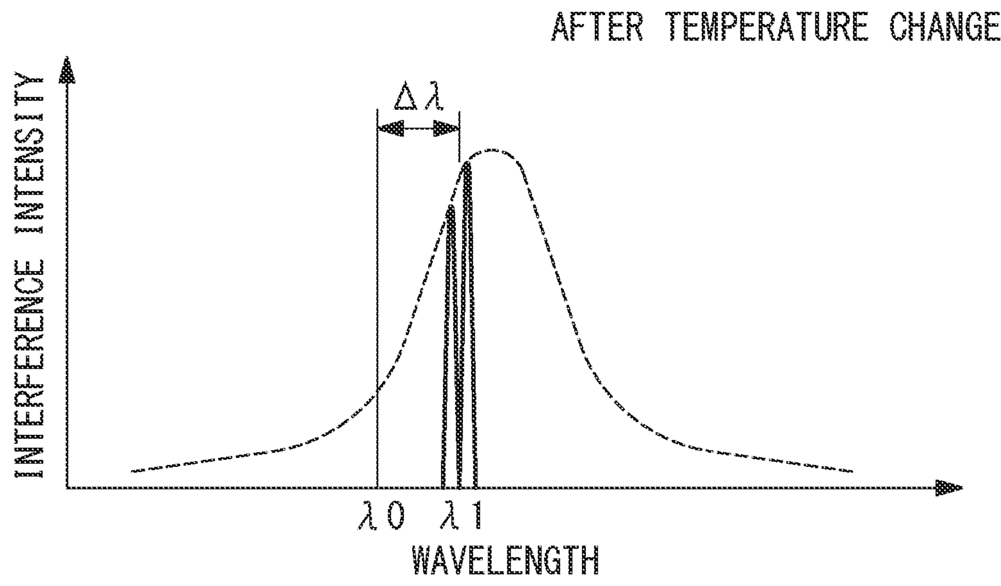
FIG. 9B is a graph showing the relationship between the wavelength and the interference intensity after temperature change.

The interference between the first measurement light U1 and the second measurement light U2 forms an interference pattern on the linear sensor 110*b*, resulting in an interference intensity distribution at a specific wavelength, as shown in FIGS. 9A and 9B. FIG. 9A shows the interference intensity distribution observed when the optical path lengths L1 and L2 are equal, and FIG. 9B shows the interference intensity distribution observed when the optical path length difference ΔL is caused by temperature change. In FIGS. 9A and 9B, the horizontal axis represents wavelength and the vertical axis represents optical intensity. The measurement light U1 and U2 are light having a wavelength width, and the wavelength at which the interference intensity distribution is generated changes according to the optical path length difference ΔL. Thus, the optical path length difference ΔL can be estimated from the amount of change in wavelength Δλ at which the interference intensity distribution occurs.

A laser treatment method using a laser treatment system 200 will now be described.

The laser treatment method of this embodiment differs from the laser treatment method described in the first embodiment in Steps S1 and S41.

In Step S1, the two optical path lengths L1 and L2 are adjusted so that they become equal while the temperature of the optical fibers 2 and 3 is uniform over the entire length. To be specific, the fine movement stage 11*a* is moved while the interference intensity distribution detected by the linear sensor 110*b* is observed, and the distance d is determined to be the reference distance d0 at which the interference intensity distribution is detected at a predetermined reference wavelength λ0.

In Step S41, the optical path length difference ΔL is measured based on the interference between the first measurement light U1 that has reciprocated along the first optical path P1 and the second measurement light U2 that has reciprocated along the second optical path P2.

To be specific, the measurement light U1 and U2 enter the first optical path P1 and the second optical path P2 from the light source unit 7 via the split-and-combine unit 8. The first measurement light U1 reciprocates along the first optical path P1 and returns to the split-and-combine unit 8. The second measurement light U2 reciprocates along the second optical path P2 and returns to the split-and-combine unit 8.

The combined light U1+U2 of the first measurement light U1 and the second measurement light U2, which are combined by the split-and-combine unit 8, is spectrally split by the diffraction grating 110*a*. Next, based on the light intensity at each wavelength detected by the linear sensor 110*b*, the wavelength λ1 at which the interference intensity distribution is generated is detected, and the amount of change in wavelength λ1 from the reference wavelength λ0, Δλ, is detected.

In the next Step S42, the amount of temperature change T in the measurement unit 2*c* corresponding to the amount of change Δλ is calculated in the computing unit 5.

Other configurations, actions, and effects of the temperature measurement device 30 are the same as those of the temperature measurement device 1, and the description thereof will therefore be omitted.

Fourth Embodiment

The temperature measurement device and medical device system according to the fourth embodiment of the present invention will now be described. In this embodiment, the same components as in the first embodiment will be denoted by the same reference numerals as the corresponding ones, and explanations thereof will be omitted.

Figure 10:
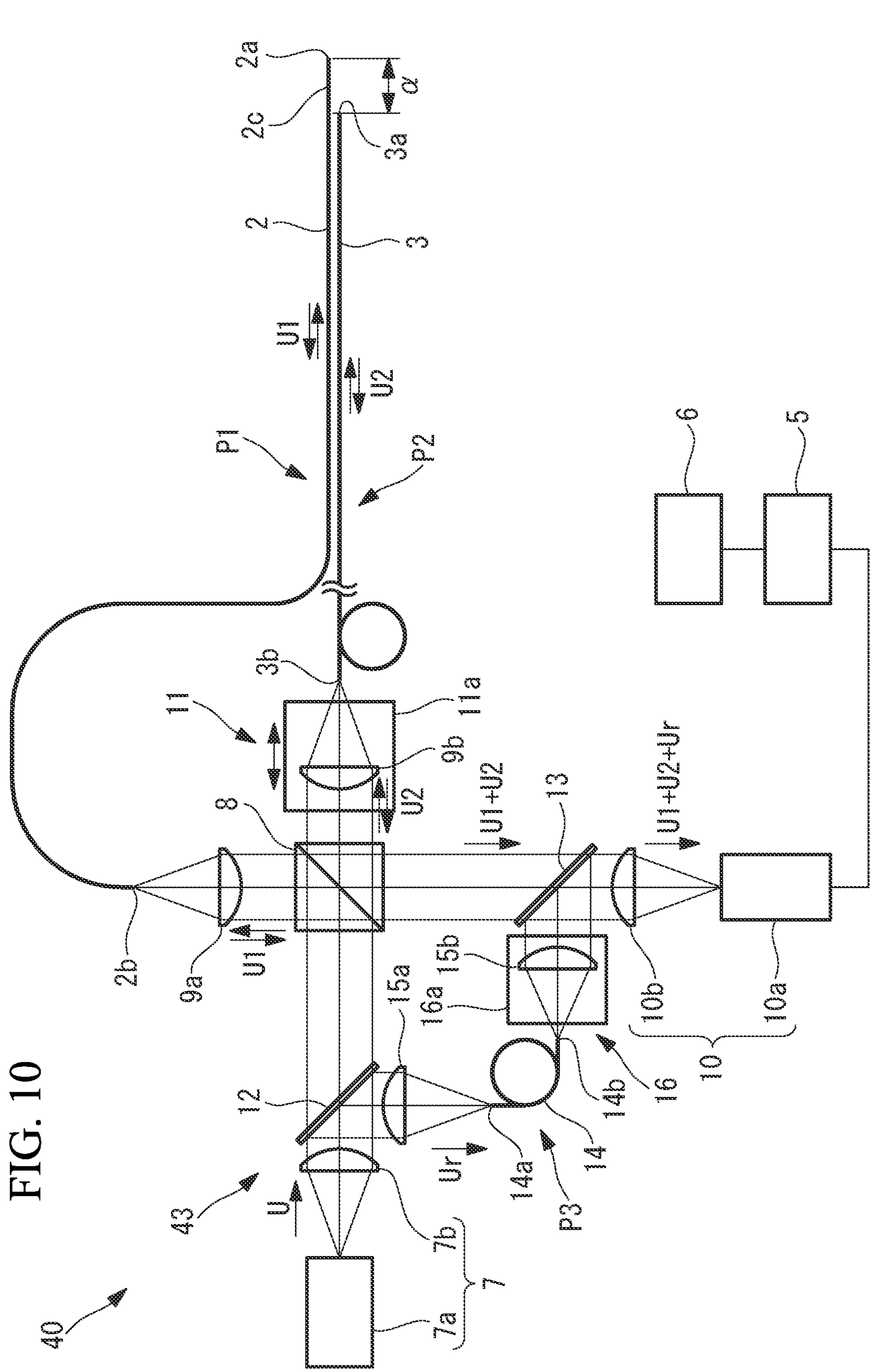
FIG. 10 is an overall configuration diagram of a temperature measurement device according to a fourth embodiment of the present invention.

The medical device system according to this embodiment includes a medical device 100 and a temperature measurement device 40. As shown in FIG. 10, the temperature measurement device 40 differs from the temperature measurement device 1 in that it has an optical path length difference measuring unit 43 instead of an optical path length difference measuring unit 4.

The temperature measurement device 40 includes a first optical fiber 2, a second optical fiber 3, an optical path length difference measuring unit 43 for measuring the optical path length difference ΔL, a computing unit 5, and a display 6.

The optical path length difference measuring unit 43 includes a light source unit 7, a split-and-combine unit 8, two couplers 9*a* and 9*b*, a detection unit 10, an optical path length adjustment mechanism 11, a reference light separating unit 12, a reference light combining unit 13, a third optical fiber 14, two couplers 15*a* and 15*b*, and another optical path length adjustment mechanism 16.

The reference light separating unit 12 is positioned between the light source unit 7 and the split-and-combine unit 8 and separates part of the measurement light U as reference light Ur. The reference light separating unit 12 is, for example, a beam sampler.

The reference light combining unit 13 is positioned between the split-and-combine unit 8 and the detection unit 10 and combines the reference light Ur with the combined light U1+U2. The reference light combining unit 13 is, for example, a combining plate such as a translucent mirror that reflects the reference light Ur and transmits the measurement light U1 and U2.

The third optical fiber 14 is positioned between the reference light separating unit 12 and the reference light combining unit 13.

The coupler 15*a* is positioned between the reference light separating unit 12 and the incident end 14*a* of the third optical fiber 14, and optically couples the reference light separating unit 12 and the incident end 14*a*. The coupler 15*b* is positioned between the reference light combining unit 13 and the emitting end 14*b* of the third optical fiber 14, and optically couples the reference light combining unit 13 and the emitting end 14*b*. To be specific, the couplers 15*a* and 15*b* are convex lenses. The coupler 15*a* focuses the reference light Ur, which is collimated light incident from the reference light separating unit 12, onto the incident end 14*a*, and the coupler 15*b* converts the reference light Ur, which is diffused light incident from the emitting end 14*b*, into collimated light which is then incident into the reference light combining unit 13.

The optical path length adjustment mechanism 16 fine-tunes the third optical path length L3 of the third optical path P3 of the reference light Ur from the reference light separating unit 12 to the reference light combining unit 13. The optical path length L3 is designed to be twice each of the optical path lengths L1 and L2. In practice, however, it is not easy to make the optical path length L3 twice each of the optical path lengths L1 and L2 due to errors in the length of the optical fiber 14.

The optical path length adjustment mechanism 16 includes a fine movement stage 16*a* that is capable of fine movement with wavelength-order resolution in the direction along the optical axis between the emitting end 14*b* and the coupler 15*b*. The coupler 15*b* is fixed to the fine movement stage 16*a*, and the fine movement stage 16*a* and the coupler 15*b* move together. Accordingly, the optical path length L3 can be fine-tuned by fine movement of the fine movement stage 16*a*.

In this embodiment, the combined light U1+U2+Ur of the first measurement light U1, the second measurement light U2, and the reference light Ur enters the photodetector 10*a*.

Figure 11A:
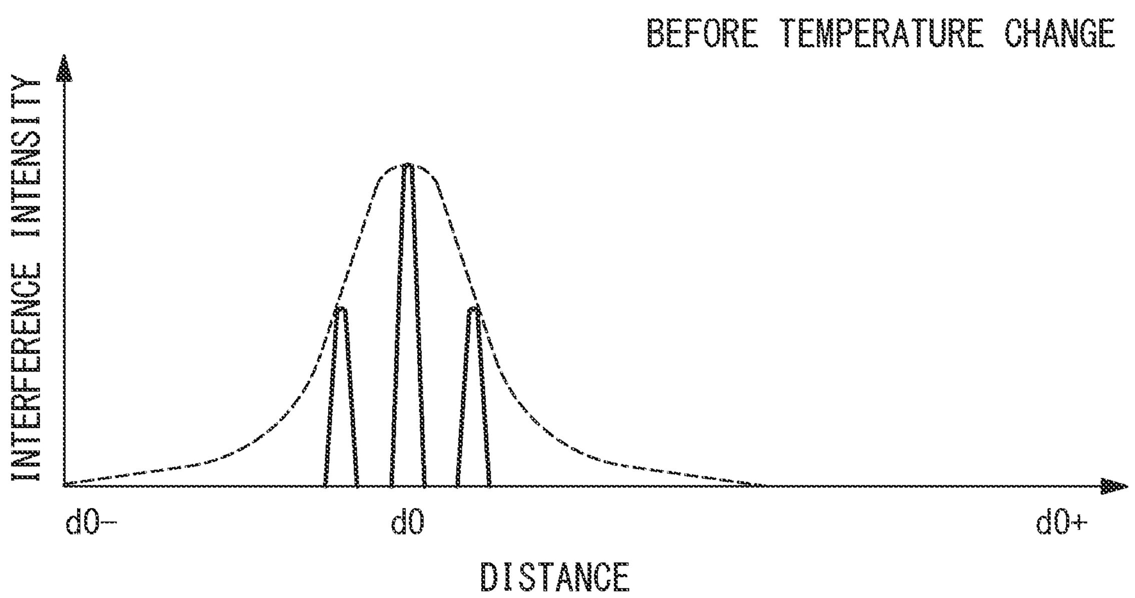
FIG. 11A is a diagram showing the relationship between the distance between an emitting end of a third optical fiber and a coupler and the interference intensity before temperature change.

When the three optical path lengths L1, L2, and L3 are equal, as shown in FIG. 11A, a single interference occurs when the three beams of light U1, U2, and U3 interfere mutually and intensify each other.

Figure 11B:
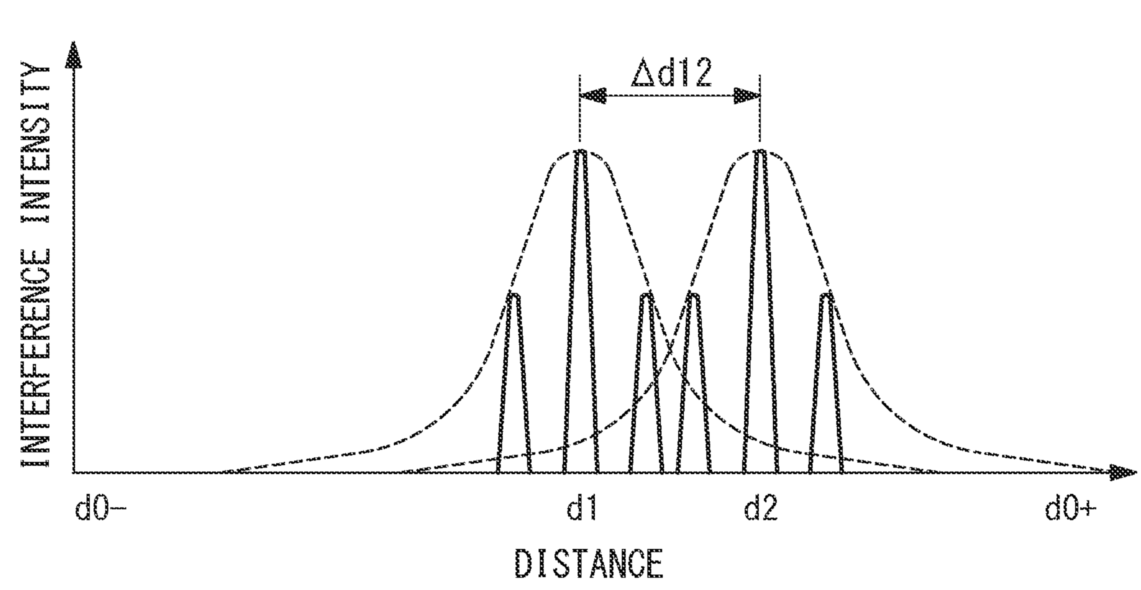
FIG. 11B is a diagram showing the relationship between the distance between the emitting end of the third optical fiber and the coupler and the interference intensity after temperature change.

On the other hand, when the optical path length difference ΔL is occurring according to the amount of temperature change T in the measurement unit 2*c*, two interference intensity distributions occur as shown in FIG. 11*b*. One interference intensity distribution is due to the interference between the first measurement light U1 and the reference light Ur, and the other interference intensity distribution is due to the interference between the second measurement light U2 and the reference light Ur. The distance difference Δd12 between the two interference intensity distributions varies according to the optical path length difference ΔL. Therefore, the temperature of the measurement unit 2*c* can be estimated from the distance difference Δd12 between the distance d1 of the fine movement stage 16*a* at which one interference intensity distribution occurs and the distance d2 of the fine movement stage 16*a* at which the other interference intensity distribution occurs. The distances d1 and d2 are the distances between the emitting end 14*b* and the coupler 15*b*.

The computing unit 5 stores an equation or table showing the relationship between the distance difference Δd12 and the amount of temperature change T, and obtains the distance difference Δd12 and the corresponding amount of temperature change T from the equation or table.

The laser treatment method using a laser treatment system 200 will now be described.

The laser treatment method of this embodiment differs from the laser treatment method that has been described in the first embodiment in Steps S1 and S41.

In Step S1, while the temperature of the optical fibers 2, 3, and 14 is uniform over the entire length, the two optical path lengths L1 and L2 are adjusted to equal using the optical path length adjustment mechanism 11, and the optical path length L3 is adjusted to twice each of the optical path lengths L1 and L2 using the optical path length adjustment mechanism 16.

In Step S41, the optical path length difference ΔL is measured based on the interference between the first measurement light U1 and the reference light Ur and the interference between the second measurement light U2 and the reference light Ur.

To be specific, the measurement light U1 and U2 enter the first optical path P1 and the second optical path P2 from the light source unit 7 via the split-and-combine unit 8. The first measurement light U1 reciprocates along the first optical path P1 and returns to the split-and-combine unit 8. The second measurement light U2 reciprocates along the second optical path P2 and returns to the split-and-combine unit 8. Also, reference light Ur enters the third optical path P3 from the light source unit 7 via the reference light separating unit 12. The reference light Ur travels along the third optical path P3 and is combined with the combined light U1+U2 in the reference light combining unit 13, and the combined light U1+U2+Ur enters the photodetector 10*a*.

When the third optical path length L3 of the reference light Ur is changed by the optical path length adjustment mechanism 16 to detect the optical path length difference ΔL, the optical path length difference between the first optical path length L1 and the third optical path length L3 is obtained from the interference intensity generated by the first measurement light U1 and the reference light Ur, as shown in FIG. 11B. At the same time, the optical path length difference between the second optical path length L2 and the third optical path length L3 is obtained from the interference intensity generated by the second measurement light U2 and the reference light Ur, and the difference Δd12 between these optical path length differences is detected. To be specific, the optical path length L3 of the reference light Ur is changed by moving the fine movement stage 16*a*, between a distance d- and a distance d+ with respect to the distance of the reciprocation of each of the first optical path length L1 and the second optical path length L2, thereby detecting the two distances d1 and d2 at which the interference intensity of the combined light U1+U2+Ur detected by the photodetector 10*a* peaks, and calculating the difference Δd12 between the distances d1 and d2.

In the next Step S42, the amount of temperature change T in the measurement unit 2*c* corresponding to the distance difference Δd12 is calculated in the computing unit 5.

In the first and second embodiments, in Step S1, it is necessary to detect and store the reference distance d0 obtained when the optical path length difference ΔL is zero. In contrast, this embodiment has an advantage over the first and second embodiments in that it does not need to store the reference distance d0.

Other configurations, actions, and effects of the temperature measurement device 40 are the same as those of the temperature measurement device 1, and the description thereof will therefore be omitted.

In the first to fourth embodiments described above, the two optical fibers 2 and 3 are positioned on the outer surface of the insertion portion 101*a* in parallel with the longitudinal direction of the insertion portion 101*a*; however, the positioning of the two optical fibers 2 and 3 is not limited to this and can be modified as needed.

Figure 12A:
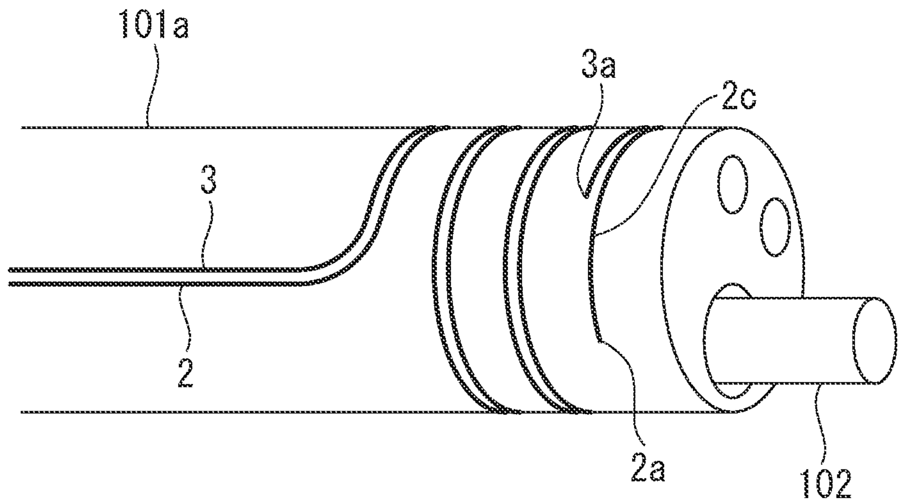
FIG. 12A is a partial configuration diagram of a modification of the medical device.

For example, as shown in FIG. 12A, the two optical fibers 2 and 3 may be spirally wound around the side surface of the distal end of the insertion portion 101*a*. The larger the length a of the measurement unit 2*c*, the more accurate the temperature measurement. Winding the optical fibers 2 and 3 in a circumferential direction allows the measurement unit 2*c* with a large length a to be easily positioned in the vicinity of the distal end of the insertion portion 101*a*, thereby easily increasing the accuracy of temperature measurement.

The optical fibers 2 and 3 need only to be positioned in the medical device 100 so that at least the measurement unit 2*c* is exposed from the medical device 100. For example, the portion closer to the proximal end than the measurement unit 2*c* may be positioned inside the insertion portion 101*a*.

Figure 12B:
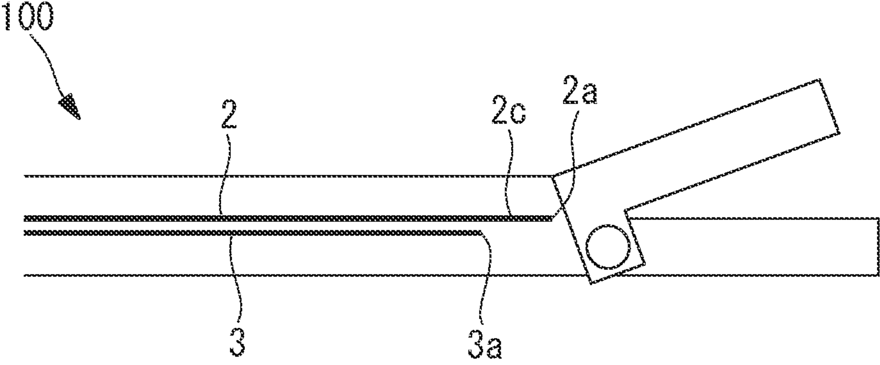
FIG. 12B is a partial configuration diagram of another modification of the medical device.
Figure 12C:
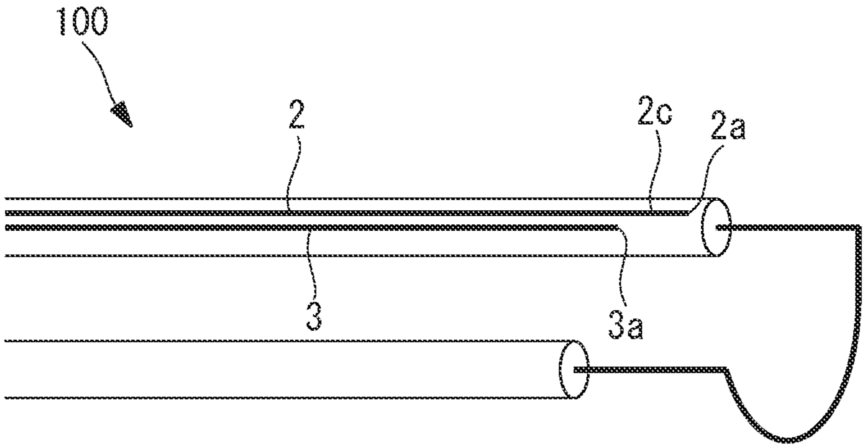
FIG. 12C is a partial configuration diagram of still another modification of the medical device.

In the first to fourth embodiments described above, the medical device 100 is supposed to be a laser treatment device; however, the temperature measurement device 1 can be applied to other medical devices 100. FIGS. 12B and 12C show examples of applying the temperature measurement device to other medical devices 100. The medical device 100 in FIG. 12B is forceps, pincer, or other treatment instrument. The medical device 100 in FIG. 12C is an electrical treatment instrument with electrodes.

REFERENCE SIGNS LIST

1, 20, 30, 40 Temperature measurement device
2 First optical fiber
2*c* Measurement unit
3 Second optical fiber
4, 41, 42, 43 Optical path length difference measuring unit
5 Computing unit
7 Light source unit
8 Split-and-combine unit
110 Detection unit
110*a*, 110*b* Spectrometer (diffraction grating, linear sensor)
11, 16 Optical path length adjustment mechanism
12 Reference light separating unit
13 Reference light combining unit
100 Medical device
200 Laser treatment system
U, U1, U2 Measurement light
Ur Reference light
V Laser beam
P1 First optical path
P2 Second optical path

The invention claimed is:

1. A temperature measurement method for measuring an ambient temperature of a long-length medical device, using a first optical fiber and a second optical fiber attached to the medical device, the first optical fiber and the second optical fiber extending in parallel with each other along a longitudinal direction of the medical device, and the first optical fiber having a distal end serving as a measurement unit extending beyond a distal end of the second optical fiber along a longitudinal direction of the first and second optical fibers, the method comprising:

measuring an optical path length difference between a first optical path including the first optical fiber and a second optical path including the second optical fiber; and calculating a temperature of the measurement unit based on the optical path length difference, wherein when temperatures of the first optical fiber and the second optical fiber are uniform, an optical path length of the first optical path and an optical path length of the second optical path are equal.

2. The temperature measurement method according to claim 1, wherein in the measuring, measuring the optical path length difference based on interference between first measurement light that has reciprocated along the first optical path and second measurement light that has reciprocated along the second optical path.

3. The temperature measurement method according to claim 2, wherein in the measuring, changing the optical path length of one of the first optical path and the second optical path, and detecting an amount of change in the optical path length of the one of the first optical path and the second optical path at which an interference intensity distribution between the first measurement light and the second measured light occurs.

4. The temperature measurement method according to claim 2, wherein in the measuring, spectrally splitting combined light of the first measurement light and the second measurement light, and detecting an amount of change in wavelength at which an interference intensity distribution between the first measurement light and the second measurement light occurs.

5. The temperature measurement method according to claim 1, wherein in the measuring, measuring the optical path length difference based on interference between first measurement light that has reciprocated along the first optical path and reference light, and interference between second measurement light that has reciprocated along the second optical path and the reference light.

6. The temperature measurement method according to claim 1, further comprising fine-tuning an optical path length of the first optical fiber or an optical path length of the second optical fiber with wavelength-order precision.

7. The temperature measurement method according to claim 1, further comprising determining a length of the measurement unit based on a temperature change amount desired to be measured.

8. A temperature measurement device that measures an ambient temperature of a long-length medical device, comprising:

a first optical fiber and a second optical fiber that are positioned in the medical device and extend in parallel with each other, the first optical fiber having a distal end serving as a measurement unit extending beyond a distal end of the second optical fiber along a longitudinal direction of the first and second optical fibers;

an optical path length difference measuring unit that measures an optical path length difference between a first optical path including the first optical fiber and a second optical path including the second optical fiber; and a processor comprising hardware configured to calculate a temperature of the measurement unit based on the optical path length difference, wherein when temperatures of the first optical fiber and the second optical fiber are uniform, an optical path length of the first optical path and an optical path length of the second optical path are equal.

9. The temperature measurement device according to claim 8, wherein the optical path length difference measuring unit comprises:

a light source unit that comprises a light source and emits measurement light;

a split-and-combine unit that comprises a splitter, is positioned between the light source unit and the first and second optical paths, splits the measurement light into first measurement light traveling along the first optical path and second measurement light traveling along the second optical path, and combines the first measurement light that has reciprocated along the first optical path and the second measurement light that has reciprocated along the second optical path; and a detection unit that detects an intensity of combined light of the first measurement light and the second measurement light that have been combined by the split-and-combine unit.

10. The temperature measurement device according to claim 9, further comprising an optical path length adjustment mechanism that comprises a stage and adjusts the optical path length of one of the first optical path and the second optical path.

11. The temperature measurement device according to claim 9, wherein the detection unit comprises a spectrometer that spectrally splits the combined light and detects an intensity at each wavelength of the combined light.

12. The temperature measurement device according to claim 9, wherein the optical path length difference measuring unit comprises:

a reference light separating unit that comprises a beam sampler and separates part of the measurement light as reference light; and a reference light combining unit that comprises a combining plate, is positioned between the split-and-combine unit and the detection unit, and combines the reference light with the combined light, the detection unit detects an intensity of a combined light of the first measurement light, the second measurement light, and the reference light that have been combined by the reference light combining unit, and an optical path length of a third optical path along which the reference light travels from the reference light separating unit to the reference light combining unit is equal to the optical path length of the first optical path and the optical path length of the second optical path.

13. The temperature measurement device according to claim 8, further comprising an optical path length adjustment mechanism that comprises a stage and fine-tunes an optical path length of the first optical fiber or an optical path length of the second optical fiber with wavelength-order precision.

14. The temperature measurement device according to claim 8, a length of the measurement unit is determined based on a temperature change amount desired to be measured.

15. A laser treatment method comprising:

preparing a medical device equipped with a first optical fiber and a second optical fiber, the first optical fiber and the second optical fiber extending in parallel with each other and the first optical fiber having a distal end serving as a measurement unit extending beyond a distal end of the second optical fiber along a longitudinal direction of the first and second optical fibers;

positioning the medical device with respect to a treatment target;

projecting a laser beam from the medical device to the treatment target; and measuring an ambient temperature of the medical device, wherein the measuring comprises:

measuring an optical path length difference between a first optical path including the first optical fiber and a second optical path including the second optical fiber; and calculating a temperature of the measurement unit based on the optical path length difference, and when temperatures of the first optical fiber and the second optical fiber are uniform, an optical path length of the first optical path and an optical path length of the second optical path are equal.

16. The laser treatment method according to claim 15, further comprising modulating an irradiation amount of the laser beam projected onto the treatment target when the temperature of the measurement unit is equal to or more than a predetermined threshold.

17. The laser treatment method according to claim 16, wherein in the modulating, stopping a projection of the laser beam.

18. The laser treatment method according to claim 16, wherein in the modulating, changing a position of the medical device.

19. The laser treatment method according to claim 18, wherein in the changing, moving the medical device away from the treatment target.

20. The laser treatment method according to claim 15, further comprising fine-tuning an optical path length of the first optical fiber or an optical path length of the second optical fiber with wavelength-order precision.

* * * * *